(12) United States Patent
Huang et al.

(10) Patent No.: US 8,648,396 B2
(45) Date of Patent: Feb. 11, 2014

(54) MICROSYSTEM FOR ANALYZING BLOOD

(75) Inventors: I-Yu Huang, Kaohsiung (TW);
Chia-Hsu Hsieh, Yunlin (TW)

(73) Assignee: Industrial Technology Research Institute, Hsinchu (TW)

( * ) Notice: Subject to any disclaimer, the term of this patent is extended or adjusted under 35 U.S.C. 154(b) by 237 days.

(21) Appl. No.: 12/982,556

(22) Filed: Dec. 30, 2010

(65) Prior Publication Data

US 2012/0091512 A1  Apr. 19, 2012

(30) Foreign Application Priority Data

Oct. 18, 2010 (TW) .............................. 99135478 A

(51) Int. Cl.
  *G01N 27/403* (2006.01)
(52) U.S. Cl.
  USPC ..... 257/253; 257/252; 257/414; 257/E29.255
(58) Field of Classification Search
  None
  See application file for complete search history.

(56) References Cited

U.S. PATENT DOCUMENTS

| | | | |
|---|---|---|---|
| 4,592,824 A | 6/1986 | Smith et al. | |
| 6,645,368 B1 | 11/2003 | Beaty et al. | |
| 2006/0197118 A1 | 9/2006 | Migliorato et al. | |
| 2007/0155037 A1 | 7/2007 | Chou et al. | |
| 2008/0061323 A1* | 3/2008 | Yazawa et al. | 257/253 |
| 2009/0266712 A1 | 10/2009 | Chou et al. | |

FOREIGN PATENT DOCUMENTS

| | | |
|---|---|---|
| CN | 1303478 A | 7/2001 |
| JP | 59-206756 | 11/1984 |
| JP | 62-250353 | 10/1987 |
| TW | 200726972 | 7/2007 |
| TW | 200846659 A | 12/2008 |
| TW | 200944789 | 11/2009 |
| TW | 201024723 | 7/2010 |
| TW | 201024723 A | 7/2010 |
| WO | 9429711 A1 | 12/1994 |
| WO | 2009064166 A2 | 5/2009 |

OTHER PUBLICATIONS

English abstracts of TW 200726972, 200944789, and 201024723.
I-Yu Huang et al., "Improvement of integrated Ag/AgCl thin-film electrodes by KCl-gel coating for ISFET applications," Sensors and Actuators B, 2003, vol. 94, pp. 53-64.
Chang-Soo Lee et al., "Ion-Sensitive Field-Effect Transistor for Biological Sensing," Sensors, 2009, vol. 9, pp. 7111-7131.

(Continued)

*Primary Examiner* — Benjamin Sandvik
*Assistant Examiner* — Leslie Pilar Cruz
(74) *Attorney, Agent, or Firm* — WPAT, P.C.; Anthony King; Kay Yang

(57) ABSTRACT

The present disclosure utilizes the MEMS (Micro Electro Mechanical Systems) process and packaging method to produce a microsystem for analyzing blood which is capable of detecting several kinds of ions. The microsystem for analyzing blood has a miniaturized reference electrode, so size of the microsystem can be greatly reduced. The microsystem further has a gate detecting area larger than a conventional planar ISE or a conventional ISFET does, so interference with signals can be avoided, and packaging difficulty and blood leakage can be reduced. Therefore, the microsystem is thin and small, reacts rapidly, and has a high accuracy, and a high compatibility with IC (integrated circuit) process. In addition, the microsystem has high stability of long-term potential, low offset-potential characteristics, low alternating current impedance, high stability of dynamic reference potential, low electrochemical noises and high reproducibility of the electrode.

12 Claims, 3 Drawing Sheets

(56) References Cited

OTHER PUBLICATIONS

N. Trombly et al., "Post-CMOS electrode formation and isolation for on-chip temperature-controlled electrochemical sensors," Electronic Letters, Jan. 3, 2008, vol. 44, No. 1, pp. 29-30.
Haigang Yang et al., "A pH-ISFET Based Micro Sensor System on Chip Using Standard CMOS Technology," Fifth International Workshop on System-on-Chip for Real-Time Applications, 2005. Proceedings., Jul. 2005, pp. 180-183.
Peter Kim et al., "An Electrochemical Interface for Integrated Biosensors," Sensors Proceedings of IEEE, Oct. 2003, vol. 2, pp. 1036-1040.
English Abstracts of JP 59-206756 and 62-250353.
Office Action issued on Mar. 12, 2013 by SIPO for the corresponding CN Patent Application No. 201010553972.5, which cites the above.
English translation of foreign reference TW201024723 and CN1303478A.
Schefer, et al., "Neutral carrier based calciunn(2+)-selective electrode with detection limit in the sub-nanomolar range", Analytical Chemistry, vol. 58, Iss.11, pp. 2282-2285(1986).
Calvo, et al., "Use of sequential injection analysis to construct an electronic-tongue: Application to multidetermination employing the transient response of a potentiometric sensor array", Analytica Chimica Acta, vol. 600, Iss.1-2, pp. 97-104(2007).
Office Action and the Search Report issued on Jun. 26, 2013 by TIPO for the corresponding TW Patent Application No. 099135478 which cites TW201024723A, WO94/29711A1, US2008/0061323A1, and TW200846659A.
English translation of foreign reference TW201024723A.
English translation of foreign reference TW200846659A.
Office Action for corresponding CN Patent Application No. 201010553972.5 dated Sep. 29, 2013.

* cited by examiner

MICROSYSTEM FOR ANALYZING BLOOD

BACKGROUND

1. Technical Field

The present disclosure relates to a microsystem for analyzing blood, and more particularly to a microsystem having miniaturized AgCl (silver chloride) reference electrode for analyzing blood.

2. Description of the Related Art

In recent years, because of rapid development of bioinformatics analysis in the fields of hematology, biochemistry and microbiology, the need for important care testing analysis system increases. Important care testing devices miniaturized by utilizing existing IC (integrated circuit) or MEMS (Micro Electro Mechanical Systems) technology have the following advantages: shorter reaction time, less sample requirements, smaller size, lower power consumption and lower production cost.

There is demand for a microsystem for analyzing blood which is capable of simultaneously detecting the concentration of ions, such as $Na^+$, $K^+$, $H^+$, $Ca^{2+}$ and $NH_4^+$ in human serum. The data of the concentration of the ions provides very important reference information when medical staff takes care of critically ill patients.

SUMMARY

The present disclosure is directed to a microsystem for analyzing blood, which comprises: an integrated structure, a plurality of ion detecting membranes, a packaging structure and a conductive material. The integrated structure has a micro reference electrode, a plurality of extended gate field effect transistor (EGFET) elements and a circuit, wherein each extended gate field effect transistor (EGFET) element has a source extension, a drain extension and a gate extension, the gate extensions are disposed at the periphery of the micro reference electrode and essentially separated from the micro reference electrode by a same distance, and the circuit electrically connects the source extensions or the drain extensions. The ion detecting membranes are disposed on a surface of the gate extensions. The packaging structure is integrated with the integrated structure and has a plurality of first through holes, a plurality of second through holes, a third through hole, a fourth through hole and a fifth through hole, the first through holes corresponding to the ion detecting membranes, the second through holes corresponding to the source extensions or the drain extensions which are not electrically connected by the circuit, the third through hole corresponding to an extension of the source extensions or the drain extensions which is electrically connected by the circuit, the fourth and fifth through hole being disposed at a corresponding position above the micro reference electrode. The conductive material is disposed in the fourth through hole and contacts the micro reference electrode.

DETAILED DESCRIPTION

Figure 1:
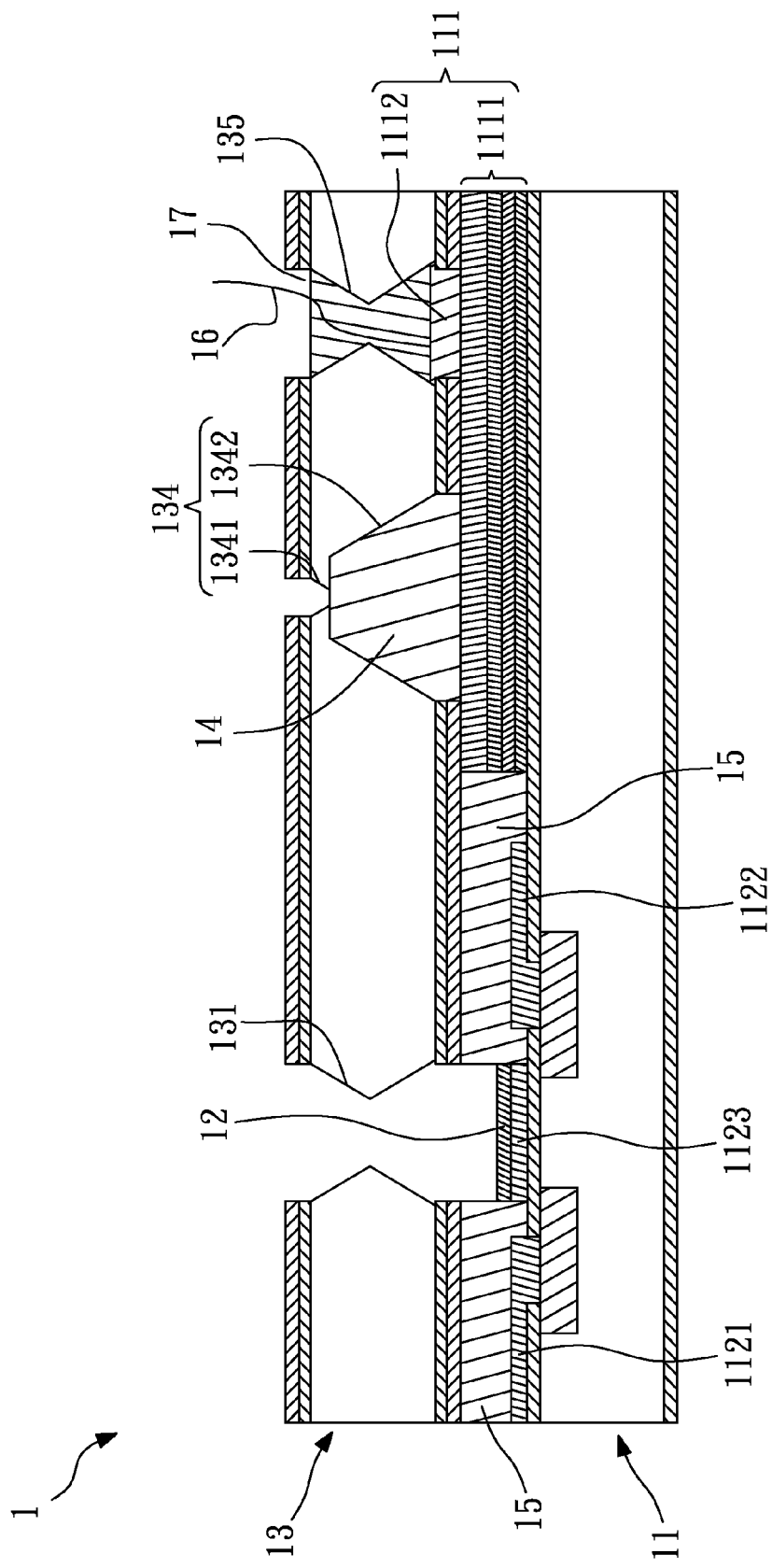
FIG. 1 is a partial cross-sectional view of a microsystem for analyzing blood according to the present disclosure.
Figure 2:
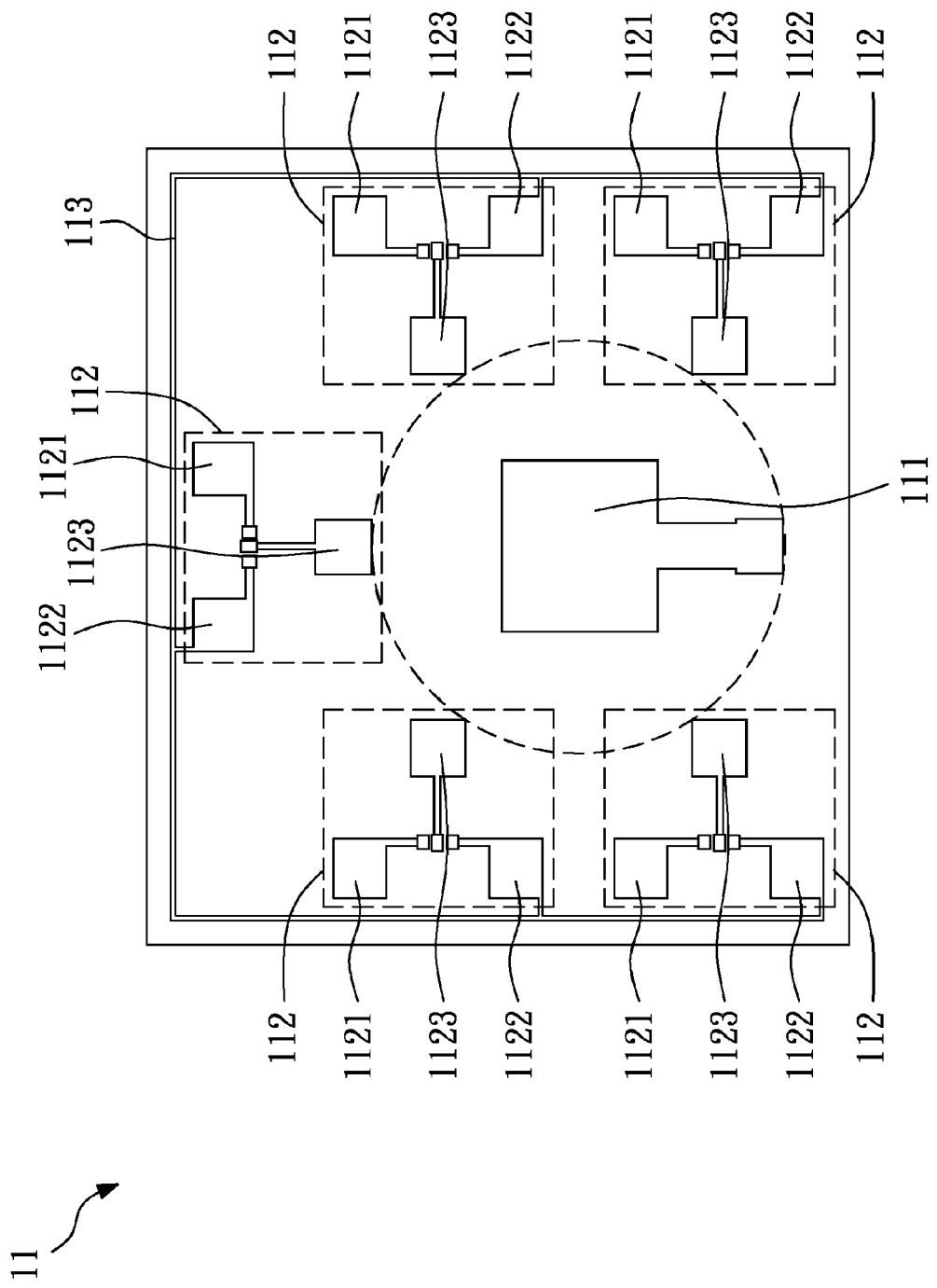
FIG. 2 is a schematic view of an integrated structure of the microsystem for analyzing blood according to the present disclosure.
Figure 3:
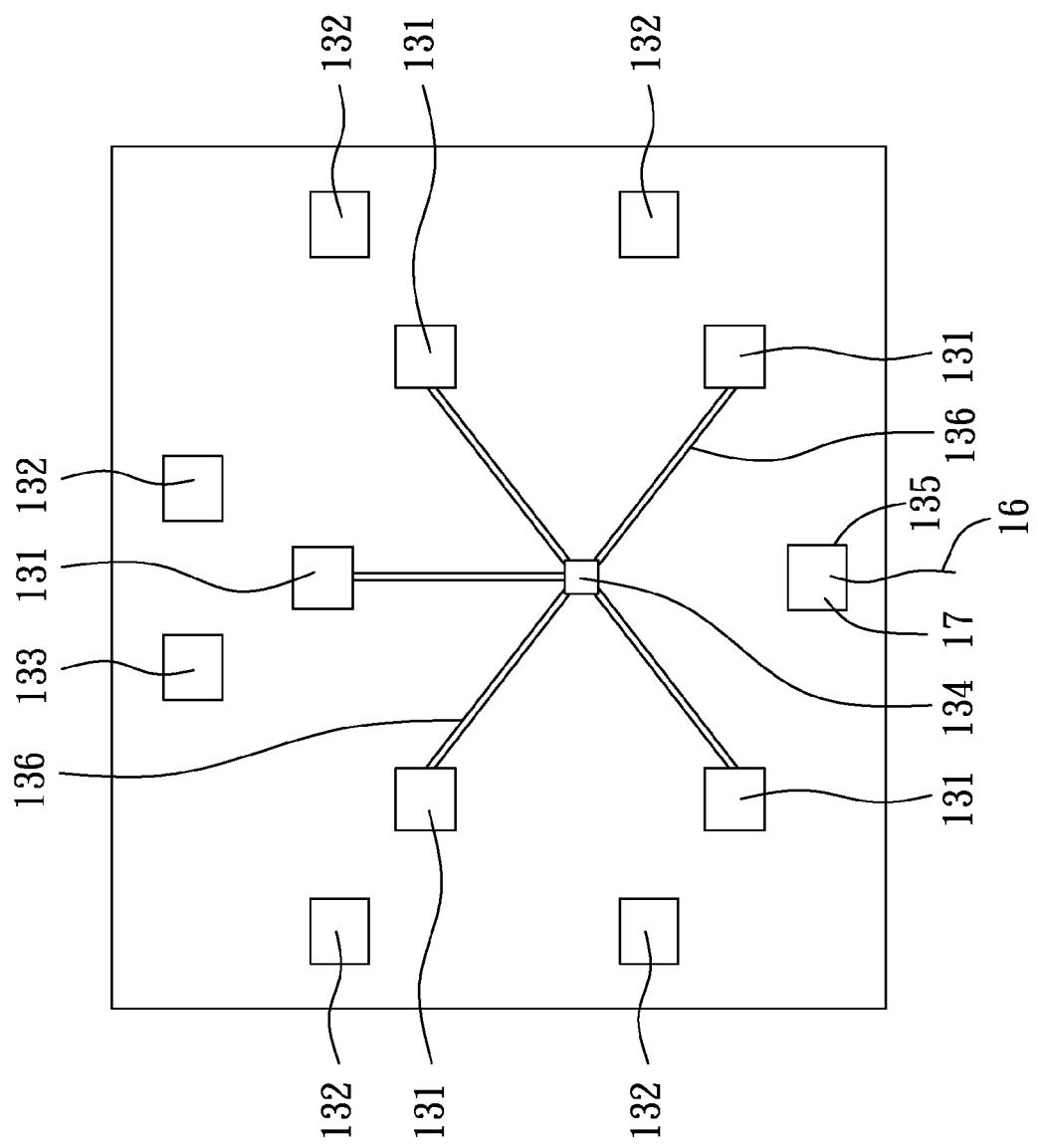
FIG. 3 is a top view of the microsystem for analyzing blood according to the present disclosure.

FIG. 1 shows a partial cross-sectional view of a microsystem for analyzing blood according to the present disclosure; FIG. 2 shows a schematic view of an integrated structure of the microsystem for analyzing blood according to the present disclosure; and FIG. 3 shows a top view of the microsystem for analyzing blood according to the present disclosure. As shown in FIGS. 1 to 3, the microsystem 1 for analyzing blood according to the present disclosure comprises: an integrated structure 11, a plurality of ion detecting membranes 12, a packaging structure 13 and a conductive material 14.

The integrated structure 11 may be a silicon chip or a glass chip. The integrated structure 11 has a micro reference electrode 111, a plurality of extended gate field effect transistor (EGFET) elements 112 and a circuit 113. Each extended gate field effect transistor (EGFET) element 112 has a source extension (extending electrode) 1121, a drain extension (extending electrode) 1122 and a gate extension (gate detecting area) 1123. The source extensions 1121, the drain extensions 1122 and the gate extensions 1123 are connected to the source, drain and gate of the extended gate field effect transistor (EGFET) elements 112. The gate extensions 1123 are disposed at the periphery of the micro reference electrode 111 and essentially separated from the micro reference electrode 111 by a same distance, and the circuit 113 electrically connects the source extensions 1121 or the drain extensions 1122.

In the embodiment, in the layout design of the integrated structure 11, the micro reference electrode 111 is disposed at the central area of the integrated structure 11, and five ion detectors (extended gate field effect transistor (EGFET) element 112/ion detecting membrane 12) surround the micro reference electrode 111 in a circular layout. The distance between the micro reference electrode 111 and each gate extension (gate detecting area) 1123 of the extended gate field effect transistor (EGFET) element 112 are almost the same (as shown by the dotted circle in FIG. 2). Therefore, not only can the error resulting from the unequal distance between the micro reference electrode 111 and the gate extension 1123 of the extended gate field effect transistor (EGFET) element 112 be reduced, but also the yield rate of packaging can be increased (because the cavity of the packaging structure 13 can be distributed evenly).

The source extension 1121 and the drain extension 1122 are used as extending electrodes, so as to electrically connect the source and the drain of the extended gate field effect transistor (EGFET) element 112 and form a larger gate detecting area, so that interference with signals and packaging difficulty resulting from the blood to be detected being too close to the source and the drain can be avoided, and blood leakage and electrochemical noises can be reduced.

In the embodiment, the micro reference electrode 111 has a reference electrode body 1111 and an electrically connecting junction 1112, and the electrically connecting junction 1112 is formed on the reference electrode body 1111. The reference electrode body 1111 comprises a Ti (titanium) layer, a Pd (palladium) layer, a Ag (silver) layer and a AgCl (silver chloride) layer in order, and the AgCl (silver chloride) layer contacts the electrically connecting junction 1112. The ion detecting membranes 12 are disposed on a surface of the gate extensions 1123.

The ion detecting membrane 12 is an ion selective membrane (ISM). In the embodiment, the ion selective membrane (ISM) is a $H^+$ selective membrane, a $Ca^{2+}$ selective membrane, a $K^+$ selective membrane, a $Na^+$ selective membrane or a $NH_4^+$ selective membrane.

In the embodiment, the $H^+$ selective membrane is a $Ta_2O_5$ (tantalum oxide) membrane, and the ingredients of the $Ca^{2+}$ selective membrane, the $K^+$ selective membrane, the $Na^+$ selective membrane or the $NH_4^+$ selective membrane comprise an ionophore, a plasticizer, an ionic additive, a polymer and an organic solvent.

Ionophore is an important reference ion in blood detection sample. The ionophore can be used to judge if there is any critically ill patients, by utilizing the size of the structure and the charged quantity of a material, in which the same kind of ion may pass through the membrane to react and change electric property of the ion selective membrane (ISM). The polymer encapsulates the ionophore, so that the ion selective membrane (ISM) comprises the ionophore. The plasticizer is used to adjust the curing degree of the polymer; if the polymer is too soft, the ionophore can not stay in the ion selective membrane (ISM), and if the polymer is too hard, the ions to be analyzed cannot diffuse in the ion selective membrane (ISM). The ionic additive with appropriate proportion can further increase the charged property of the ion selective membrane (ISM), so that the ion selective membrane (ISM) is more likely to capture the free-ion. The organic solvent helps make a better mixture of the ionophore, the plasticizer, the ionic additive and the polymer.

In the embodiment, the ionophore of the $Ca^{2+}$ selective membrane is ETH129 (Calcium Ionophore II, produced by Fluka), the plasticizer is NPOE (produced by Alfa Aesar), the ionic additive is K-TpClPB (produced by Alfa Aesar), the polymer is PVC (polyvinyl chloride) (produced by Fluka), and the organic solvent is THF (tetrahydrofuran) (produced by Mallinckrodt). The ionophore of the $K^+$ selective membrane is valinomycin (produced by Dojindo), the plasticizer is DOS (produced by Fluka), the ionic additive is K-TpClPB (produced by Alfa Aesar), the polymer is PVC (polyvinyl chloride), and the organic solvent is THF (tetrahydrofuran). The ionophore of the $Na^+$ selective membrane is Sodium ionophore X (produced by Fluka), the plasticizer is NPOE, the ionic additive is K-TpClPB, the polymer is PVC (polyvinyl chloride), and the organic solvent is THF (tetrahydrofuran). The ionophore of the $NH_4^+$ selective membrane is TD19C6 (produced by Dojindo), the plasticizer is BBPA (produced by Fluka), the ionic additive is KTCPB (produced by Alfa Aesar), the polymer is PVC (polyvinyl chloride), and the organic solvent is THF (tetrahydrofuran).

In the embodiment, the ionophore ETH129 of the $Ca^{2+}$ selective membrane is 1.0 wt %, the plasticizer NPOE is 65.6 wt %, the ionic additive K-TpClPB is 0.6 wt %, the polymer PVC (polyvinyl chloride) is 32.8 wt %, and the content of the organic solvent THF (tetrahydrofuran) is 1.3 mL. The ionophore valinomycin of the $K^+$ selective membrane is 1.1 wt %, the plasticizer DOS is 67.6 wt %, the ionic additive K-TpClPB is 0.6 wt %, the polymer PVC (polyvinyl chloride) is 30.7 wt %, and the content of the organic solvent THF (tetrahydrofuran) is 1.2 mL. The ionophore Sodium ionophore X of the $Na^+$ selective membrane is 0.7 wt %, the plasticizer NPOE is 66.1 wt %, the ionic additive K-TpClPB is 0.2 wt %, the polymer PVC (polyvinyl chloride) is 33.0 wt %, and the content of the organic solvent THF (tetrahydrofuran) is 1.9 mL. The ionophore TD19C6 of the $NH_4^+$ selective membrane is 3.0 wt %, the plasticizer BBPA is 67.0 wt %, the content of the ionic additive KTCPB is 0.5 mg, the polymer PVC (polyvinyl chloride) is 30.0 wt %, and the content of the organic solvent THF (tetrahydrofuran) is 0.5 mL.

The packaging structure 13 may be a silicon chip or a glass chip, and is integrated with the integrated structure 11. In the embodiment, the integrated structure 11 and the packaging structure 13 are integrated by a bonding material 15. The bonding material 15 is preferably epoxy resin. The packaging structure 13 has a plurality of first through holes 131, a plurality of second through holes 132, a third through hole 133, a fourth through hole 134 and a fifth through hole 135.

The first through holes 131 correspond to the ion detecting membranes 12; the second through holes 132 correspond to the source extensions 1121 or the drain extensions 1122 which are not electrically connected by the circuit 113; the third through hole 133 corresponds to an extension of the source extensions 1121 or the drain extensions 1122 which is electrically connected by the circuit 113; and the fourth through hole 134 and the fifth through hole 135 are disposed at a corresponding position above the micro reference electrode 111.

In the embodiment, the second through holes 132 correspond to the source extensions 1121, and the third through hole 133 in FIG. 3 corresponds to the drain extension 1122 at the top of FIG. 2. The circuit 113 electrically connects the drain extensions 1122, and less through holes are needed to be formed in the packaging structure 13, so packaging is much simpler, and the packaging structure 13 is not easily fragmented and is more easy to manufacture. Each extended gate field effect transistor (EGFET) element 112 is electrically connected to the corresponding drain extension 1122 by a wire through a third through hole 133 and electrically connected to the corresponding source extension 1121 by wires through each second through hole 132, and detection of plural kinds of ions can be conducted.

The fourth through hole 134 has a first cavity 1341 and a second cavity 1342, and the fifth through hole 135 corresponds to the electrically connecting junction 1112. In the embodiment, the second cavity 1342 is larger than the first cavity 1341 and faces the micro reference electrode 111, and the first cavity 1341 and the second cavity 1342 taper inward from two side surfaces of the packaging structure 13 and communicate with each other.

The conductive material 14 is disposed in the fourth through hole 134 and contacts the micro reference electrode 111. In the embodiment, the conductive material 14 is a KCl (potassium chloride) gel and is disposed in the second cavity 1342, and the first cavity 1341 exposes part of the conductive material 14.

Preferably, the surface of the packaging structure 13 further comprises a plurality of grooves 136. The grooves 136 are connected to the fourth through hole 134 (disposed at a corresponding position above the conductive material 14) and the first through holes 131 (disposed at a corresponding position above the ion detecting membranes 12). When the blood to be detected is dropped in the fourth through hole 134, the grooves 136 will guide the blood to be detected into each first through hole 131 (detecting area), so the amount needed for detection is less, and the blood will flow into each first through hole 131 (detecting area) more smoothly.

When the ion detecting membranes 12 contact the blood to be detected, the ion detecting membranes 12 detect the interface potential resulting from the blood to be detected and the surface of the ion detecting membranes 12, so as to detect the concentration of the ion in the blood to be detected.

In the embodiment, the microsystem 1 for analyzing blood further comprises a wire 16 and a molding compound 17 encapsulating the wire 16. One end of the wire 16 is electrically connected to the micro reference electrode 111, and the other end of the wire 16 can be used to connect to an external circuit. In the embodiment, the wire 16 is electrically connected to the electrically connecting junction 1112 of the micro reference electrode 111. The molding compound 17 is disposed in the fifth through hole 135 so as to encapsulate, fix and protect the wire 16. In which, the molding compound 17 may be an ultraviolet (UV) gel.

The present disclosure utilizes the MEMS (Micro Electro Mechanical Systems) process and packaging method to produce a microsystem 1 for analyzing blood having ion detecting membrane which is capable of detecting several kinds of ions ($H^+$, $Ca^{2+}$, $K^+$, $Na^+$ and $NH_4^+$ so as to detect $H^+$, $Ca^{2+}$, $K^+$, $Na^+$ and $NH_4^+$ ions in blood; furthermore, the microsystem 1 for analyzing blood according to the present disclosure has a miniaturized solid-state reference electrode (the micro reference electrode 111), so the microsystem can be miniaturized to about one of hundreds of the size of a conventional ion detector. Therefore, the microsystem 1 for analyzing blood according to the present disclosure has the following advantages: (i) the microsystem is made by planarization process technology, so the microsystem is thin and small, reacts rapidly, and has a high accuracy; (ii) the microsystem can be mass produced, so the production cost is low; (iii) the microsystem has a high compatibility with IC (integrated circuit) process, so it can be widely applied.

Moreover, the microsystem 1 for analyzing blood according to the present disclosure has excellent electrochemial characteristics: (i) high stability of long-term potential: low electrode potential float measured in thirty thousand seconds (~5 mV); (ii) low offset-potential characteristics (−7 mV); (iii) low alternating current resistance (1.5 kΩ; (iv) low phase shift (8.98)°; (v) as proved by cyclic voltammetry, the micro reference electrode is a reversible and non-polarizable electrode and provides high stability of dynamic reference potential; (vi) low electrochemistry noises; (vii) high reproducibility of the electrode (±3.1 mV).

While several embodiments of the present disclosure have been illustrated and described, various modifications and improvements can be made by those skilled in the art. The embodiments of the present disclosure are therefore described in an illustrative but not restrictive sense. It is intended that the present disclosure should not be limited to the particular forms as illustrated, and that all modifications which maintain the spirit and scope of the present invention are within the scope defined in the appended claims.

What is claimed is:

1. A microsystem for analyzing blood, comprising:
   an integrated structure, having a micro reference electrode, a plurality of extended gate field effect transistor (EG-FET) elements and a circuit, wherein each extended gate field effect transistor (EGFET) element has a source extension, a drain extension and a gate extension, the gate extensions are disposed at the periphery of the micro reference electrode and essentially separated from the micro reference electrode by a same distance, and the circuit electrically connects the source extensions or the drain extensions;
   a plurality of ion detecting membranes, disposed on a surface of the gate extensions;
   a packaging structure, assembled with the integrated structure, wherein the packaging structure has a plurality of first through holes, a plurality of second through holes, a third through hole, a fourth through hole and a fifth through hole, the first through holes corresponding to the ion detecting membranes, the second through holes corresponding to the source extensions or the drain extensions which are not electrically connected by the circuit, the third through hole corresponding to an extension of the source extensions or the drain extensions which is electrically connected by the circuit, and the fourth through hole and the fifth through hole being disposed at a corresponding position above the micro reference electrode; and
   a conductive material, disposed in the fourth through hole and contacting the micro reference electrode;
   wherein the micro reference electrode has a reference electrode body and an electrically connecting junction, the electrically connecting junction is formed on the reference electrode body, and the electrically connecting junction corresponds to the fifth through hole.

2. The microsystem for analyzing blood as claimed in claim 1, wherein the reference electrode body comprises a Ti (titanium) layer, a Pd (palladium) layer, a Ag (silver) layer and a AgCl (silver chloride) layer in this order, and the AgCl (silver chloride) layer contacts the electrically connecting junction.

3. The microsystem for analyzing blood as claimed in claim 1, wherein the conductive material is a KCl (potassium chloride) gel.

4. The microsystem for analyzing blood as claimed in claim 1, wherein the fourth through hole has a first cavity and a second cavity, the second cavity facing the micro reference electrode, and the first cavity and the second cavity tapering inward from two side surfaces of the packaging structure respectively and communicating with each other.

5. The microsystem for analyzing blood as claimed in claim 4, wherein the conductive material is disposed in the second cavity, and the first cavity exposes part of the conductive material.

6. The microsystem for analyzing blood as claimed in claim 1, further comprising a wire electrically connected to the micro reference electrode.

7. The microsystem for analyzing blood as claimed in claim 6, further comprising a molding compound disposed in the fifth through hole, and the molding compound encapsulates and fixes the wire.

8. The microsystem for analyzing blood as claimed in claim 1, wherein the ion detecting membrane is an ion selective membrane (ISM).

9. The microsystem for analyzing blood as claimed in claim 8, wherein the ion selective membrane (ISM) is a $H^+$ selective membrane, a $Ca^{2+}$ selective membrane, a $K^+$ selective membrane, a $Na^+$ selective membrane or a $NH_4^+$ selective membrane.

10. The microsystem for analyzing blood as claimed in claim 9, wherein the $H^+$ selective membrane is a $Ta_2O_5$ (tantalum oxide) membrane, and the ingredients of the $Ca^{2+}$ selective membrane, the $K^+$ selective membrane, the $Na^+$ selective membrane or the $NH_4^+$ selective membrane comprise an ionophore, a plasticizer, an ionic additive, a polymer and an organic solvent.

11. The microsystem for analyzing blood as claimed in claim 10, wherein the ionophore of the $Ca^{2+}$ selective membrane is ETH129, the plasticizer is NPOE, the ionic additive is K-TpClPB, the polymer is PVC (polyvinyl chloride), and the organic solvent is THF (tetrahydrofuran); the ionophore of the $K^+$ selective membrane is is valinomycin, the plasticizer is DOS, the ionic additive is K-TpClPB, the polymer is PVC (polyvinyl chloride), and the organic solvent is THF (tetrahydrofuran); the ionophore of the $Na^+$ selective membrane is Sodium ionophore X, the plasticizer is NPOE, the ionic additive is K-TpClPB, the polymer is PVC (polyvinyl chloride), and the organic solvent is THF (tetrahydrofuran); the ionophore of the $NH_4^+$ selective membrane is TD19C6, the plasticizer is BBPA, the ionic additive is KTCPB, the polymer is PVC (polyvinyl chloride), and the organic solvent is THF (tetrahydrofuran).

12. The microsystem for analyzing blood as claimed in claim 11, wherein the ionophore ETH129 of the $Ca^{2+}$ selective membrane is 1.0 wt %, the plasticizer NPOE is 65.6 wt %, the ionic additive K-TpClPB is 0.6 wt %, the polymer PVC (polyvinyl chloride) is 32.8 wt %, and the content of the organic solvent THF (tetrahydrofuran) is 1.3 mL; the ionophore valinomycin of the $K^+$ selective membrane is 1.1 wt %, the plasticizer DOS is 67.6 wt %, the ionic additive K-TpClPB is 0.6 wt %, the polymer PVC (polyvinyl chloride) is 30.7 wt %, and the content of the organic solvent THF (tetrahydrofuran) is 1.2 mL; the ionophore Sodium ionophore X of the $Na^+$ selective membrane is 0.7 wt %, the plasticizer NPOE is 66.1 wt %, the ionic additive K-TpClPB is 0.2 wt %, the polymer PVC (polyvinyl chloride) is 33.0 wt %, and the content of the organic solvent THF (tetrahydrofuran) is 1.9 mL; the ionophore TD19C6 of the $NH_4^+$ selective membrane is 3.0 wt %, the plasticizer BBPA is 67.0 wt %, the content of the ionic additive KTCPB is 0.5 mg, the polymer PVC (polyvinyl chloride) is 30.0 wt %, and the content of the organic solvent THF (tetrahydrofuran) is 0.5 mL.

\* \* \* \* \*